United States Patent [19]

Koshiishi

[11] 4,218,746
[45] Aug. 19, 1980

[54] METHOD AND APPARATUS FOR CALIBRATING ION CONCENTRATION MEASUREMENT

[75] Inventor: Kiyozo Koshiishi, Sagamihara, Japan

[73] Assignee: Olympus Optical Co., Ltd., Tokyo, Japan

[21] Appl. No.: 950,294

[22] Filed: Oct. 11, 1978

[30] Foreign Application Priority Data

Oct. 20, 1977 [JP] Japan .................................. 52-126022

[51] Int. Cl.² ...................... G06F 15/42; G01N 27/46
[52] U.S. Cl. .................................... 364/571; 364/497; 204/195 R; 204/1 T
[58] Field of Search ............... 364/571, 497, 498, 499, 364/502, 504; 422/98; 324/30 R; 204/195 R, 195 M, 195 G, 1 T, 1 H, 1 B

[56] References Cited

U.S. PATENT DOCUMENTS

| | | | |
|---|---|---|---|
| 3,600,567 | 8/1971 | Varnela | 364/498 |
| 3,824,453 | 7/1974 | Baker | 204/1 T |
| 3,862,895 | 1/1975 | King et al. | 204/195 M |
| 3,865,708 | 2/1975 | Light et al. | 204/195 M |
| 3,960,497 | 6/1976 | Acord | 364/497 |
| 4,020,329 | 4/1977 | Church et al. | 364/504 |
| 4,023,022 | 5/1977 | Mukae et al. | 364/497 |
| 4,028,534 | 6/1977 | Tucker | 364/497 |
| 4,048,041 | 9/1977 | David et al. | 204/1 T |
| 4,060,717 | 11/1977 | Sitek | 364/497 |

*Primary Examiner*—Charles E. Atkinson
*Assistant Examiner*—Gary Chin
*Attorney, Agent, or Firm*—Haseltine, Lake & Waters

[57] ABSTRACT

A method for measuring ion concentration of a sample solution by detecting a potential difference generated between an ion electrode and a reference electrode which are dipped in the sample solution, while calibrating or compensating variations in a reference point and a span due to a drift, fluctuations of temperature, humidity, voltage supply source and the like with the aid of at least two standard solutions having known ion concentrations. The method comprises a step for detecting potential differences $E_1$ and $E_2$ corresponding to the known ion concentrations $a_1$ and $a_2$ of the first and second standard solutions, respectively;

a step for calculating a proportional constant c in accordance with the following equation;

$$c = \frac{E_1 - E_2}{\log(a_1/a_2)};$$

a step for detecting a potential difference $E_x$ corresponding to an unknown ion concentration $a_x$;

a step for calculating the unknown ion concentration $a_x$ in accordance with an equation of $$a_x = a_1 \cdot 10^{\frac{E_x - E_1}{c}}$$

or $$a_x = a_2 \cdot 10^{\frac{E_x - E_2}{c}}$$

with the aid of the detected potential value $E_1$ or $E_2$, known ion concentration $a_1$ or $a_2$ and calculated constant c which have been stored in a memory and the detected potential value $E_x$. During the measurement the reference point can be simply recalibrated by detecting a potential difference $E'_1$ or $E'_2$ of the first or second standard solution and the newly detected potential value $E'_1$ or $E'_2$ is used for calculating unknown ion concentrations of subsequent sample solutions.

6 Claims, 2 Drawing Figures

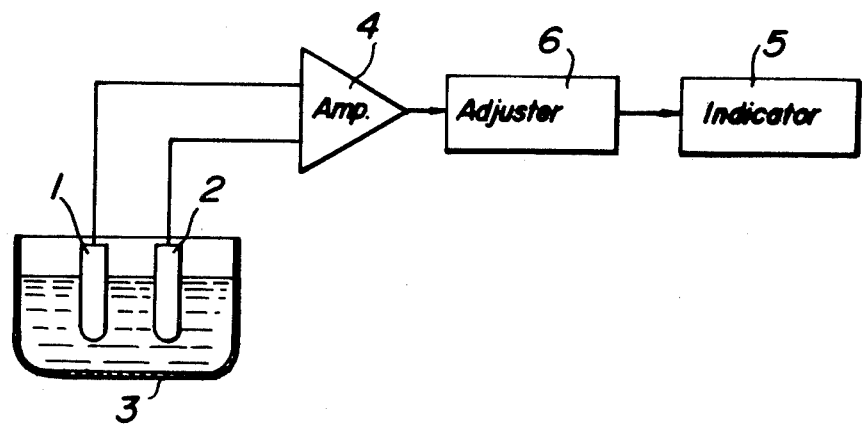
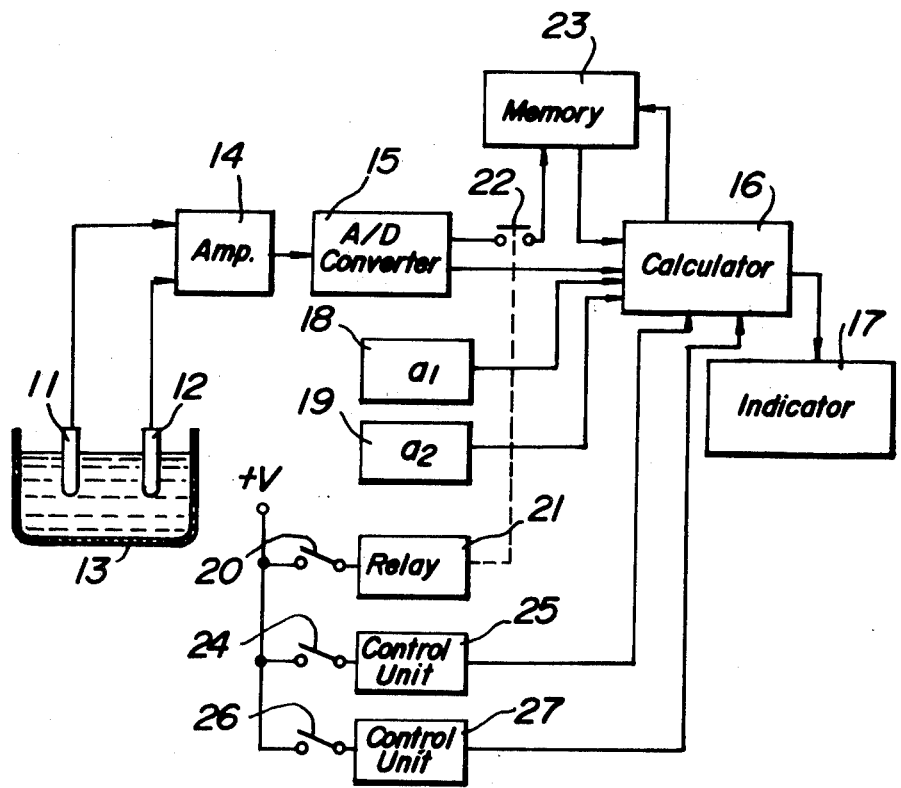

METHOD AND APPARATUS FOR CALIBRATING ION CONCENTRATION MEASUREMENT

BACKGROUND OF THE INVENTION

This invention relates generally to a method for measuring ion concentration of a sample solution by detecting a potential difference generated between an ion electrode and a reference electrode which are dipped in the sample solution, and more particularly to a method for measuring the ion concentration while calibrating or compensating variations in a reference point and a span with the aid of at least two standard solutions having known ion concentrations.

The problems encountered at the ion concentration measurement are a drift of the reference point and a deviation of the span due to disturbances such as variations of temperature, humidity and the like, and fluctuations of a voltage supply source. Such problems require calibrations or compensations of the reference point and span. In known methods the calibrations are effected with the aid of at least two standard solutions having known ion concentrations in such a manner as will be explained hereinafter with reference to FIG. 1.

FIG. 1 is a block diagram showing an ebodiment of a known ion concentration measuring apparatus. The apparatus comprises an ion electrode or a measuring electrode 1 and a reference electrode 2 which are so constructed to respond selectively to given ions to be measured. When the electrodes 1 and 2 are dipped into a solution with the given ions contained in a vessel 3, there will be generated a potential at respective electrode and a difference between these potentials is a measure of an ion concentration of the solution. This potential difference is amplified by an amplifier 4 and then is applied to an indicator 5 where the potential difference is displayed in the form of the ion concentration. Prior to the measurement, the reference point and the span have to be calibrated with the aid of an adjuster 6 inserted between the amplifier 4 and the indicator 5. Usually the adjuster 6 comprises a stage for shifting a signal level and a stage for adjusting a gain. At first the reference point is corrected with using a first standard solution. To this end the first stardard solution is introduced in the vessel 3 and a potential difference corresponding to the known ion concentration of this first standard solution is detected. The level of measuring potential difference is so adjusted by means of the adjuster 6 that the indicator 5 indicates correctly the known ion concentration. Next the span is calibrated with the aid of a second standard solution having an ion concentration which is also known, but is different from the ion concentration of the first standard solution. To this end a potential difference corresponding to the known ion concentration of the second standard solution is detected and the gain is adjusted by the adjuster 6 so that the indicator 5 indicates correctly this known ion concentration. In this manner the reference point and span are calibrated. In general, the calibration of the reference point should be effected frequently, while that of the span need not be carried out during the measurement, because the reference point is affected by the drift, but the span is hardly influenced by the drift.

The known calibration method has a defect that the reference point and the span cannot be precisely corrected, because the reference point has to be calibrated before the span calibration and thus the latter calibration inevitably causes a deviation of the reference point and the calibration of span has to be effected on the basis of uncertained reference point which has not be corrected precisely. Moreover the adjustment of the adjuster 6 is quite troublesome, because it must be performed manually while observing an indications displayed on the indicator 5. This manual operation may be effected in an automatic manner, but the automatization naturally requires a very complicated construction and a large expense. Further, in the known calibration method during the measurement the adjuster 6 has to be adjusted sometimes with using both the first and second standard solutions so as to recalibrate the reference point. Therefore a relatively long time period is required for the recalibration during the measurement.

SUMMARY OF THE INVENTION

The present invention has for its object to provide an improved method for measuring ion concentrations of sample solutions, while calibrating the reference point and the span in a simple and accurate manner with the aid of at least two standard solutions having known ion concentrations.

It is another object of the invention to provide an ion concentration measuring method in which the recalibration of the reference point during the measurement can be carried out simply and speedily while using only one of the standard solutions.

A method for measuring ion concentrations of sample solutions according to the invention comprises a step for detecting potential values $E_1$ and $E_2$ corresponding to known different ion concentrations $a_1$ and $a_2$, respectively of at least two standards solutions;

a setp for calculating a constant c with the aid of the detected potential values $E_1$ and $E_2$ and previously known ion concentration $a_1$ and $a_2$ in accordance with an equation of $$c = \frac{E_1 - E_2}{\log(a_1/a_2)};$$

a step for storing in a memory at least the calculated constant c, one of the known ion concentrations $a_k$ (=$a_1$ or $a_2$) and the detected potential value $E_k$ (=$E_1$ or $E_2$) related to said stored known ion concentration $E_k$;

a step for detecting a potential value $E_x$ corresponding to an unknown ion concentration $a_x$ of a sample solution;

a step for calculating the unknown ion concentration $a_x$ in accordance with an equation of $$a_x = a_k \cdot 10^{\frac{E_x - E_k}{c}}$$

with the aid of the calculated constant c, known ion concentration $a_k$ and its related potential value $E_k$ stored in the memory and the detected potential $E_x$; and a step for displaying the calculated ion concentration $a_x$ of the sample solution.

The invention also relates to an apparatus for measuring ion concentrations of sample solutions, which can calculate correct ion concentrations while compensating the variations of the reference point and span in a simple and accurate manner.

An apparatus for measuring ion concentrations of sample solutions according to the invention comprises means for detecting an electric potential a value of which corresponds to an ion concentration of a solution;

means for presetting known ion concentrations $a_1$ and $a_2$ of at least two standard solutions having the known different ion concentrations $a_1$ and $a_2$, respectively;

means for calculating a constant c in accordance with an equation of $$c = \frac{E_1 - E_2}{\log(a_1/a_2)},$$

wherein $E_1$ and $E_2$ are potential values derived from said detecting means in accordance with equations $E_1 = E_0 + c \log a_1$ and $E_2 = E_0 + c \log a_2$, respectively upon measurements of the standard solutions;

means for storing at least said calculated constant c, one of the detected potential values $E_k (= E_1$ or $E_2)$ and the known ion concentration $a_k$ related to the potential value $E_k$;

means for supplying the stored values and a measured potential $E_x$ derived from the detecting means upon a measurement of a sample solution having an unknown ion concentration $a_x$ to said calculating means to cause a calculation of the unknown ion concentration $a_x$ in accordance with an equation of $$a_x = a_k \cdot 10^{\frac{E_x - E_k}{c}}; \text{ and}$$

means for receiving the unknown ion concentration $a_x$ thus calculated and dispalying the same.

BRIEF DESCRIPTION OF THE DRAWINGS

FIG. 1 is a block diagram showing a known apparatus for measuring ion concentrations of sample solutions; and FIG. 2 is a block diagram illustrating an embodiment of an ion concentration measuring apparatus according to the invention.

DESCRIPTION OF THE PREFERRED EMBODIMENTS

FIG. 2 is a block diagram showing an embodiment of the apparatus for measuring ion concentrations of sample solutions according to the invention. The apparatus comprises an ion electrode 11 and a reference electrode 12 which are dipped in a solution contained in a vessel 13. Then a potential difference will be produced between the two electrodes 11 and 12. Since a combination of the electrodes 11 and 12 and the solution including one or more metallic ions constitutes an electrochemical cell, the potential difference represents an amount of ions of given kind to be measured. The produced potential difference is amplified by an amplifier 14 having a high input impedance, converted into a digital information through an analog-to-digital converter 15, and then fed to an arithmetic unit 16 to calculate a measured ion concentration.

Then the calculated ion concentration is further supplied to an indicator 17, in the present embodiment a digital indicator which displays the measured ion concentration in a digital amount.

It should be noted that the so-called following Nernst's equation holds for the relation between an ion concentration a of the solution and a potential difference E.

$$E = E_0 + c \log a.$$

At first, a first standard solution having a known ion concentration $a_1$ is introduced in the vessel 13. The known concentration $a_1$ is set manually in a preset-counter 18. The two electrodes 11 and 12 are dipped into the first standard solution and then a potential difference $E_1$ will be produced between them. In this case the Nernst's equation is as follows:

$$E_1 = E_0 + c \log a_1 \qquad (1)$$

Then a second standard solution whose ion concentration $a_2$ is also known is introduced in the vessel 13 after discharging the first standard solution therefrom. The known concentration $a_2$ of the second standard solution is stored in a preset-counter 19. The potential difference $E_2$ produced in this case is represented by the following equation (2).

$$E_2 = E_0 = c \log a_2 \qquad (2)$$

In the above two equations (1) and (2), $E_0$ is a constant potential determined by the electrodes 11 and 12, and c is a constant representing a slope of a linear function expressing a relation between the potential value E and log a. During the measurement of the potential differences $E_1$ and $E_2$ for the first and second standard solutions a switch 20 is closed to apply a voltage V to a relay 21. Thus the relay 21 is energized and its contact 22 is closed. Therefore, the digital values of the detected potential differences $E_1$ and $E_2$ are supplied to a memory 23 via the amplifier 14, the analog-to-digital coverter 15 and the closed relay contact 22. Then the constant c is calculated with using the potential values $E_1$ and $E_2$ stored in the memory 23 and the known ion concentrations $a_1$ and $a_2$ set in the preset-counters 18 and 19, respectively. To this end a switch 24 is closed to energize a control unit 25 which commands the arithmetic unit 16 to calculate the constant c according to the following equation (3) which is derived from the equations (1) and (2), $$C = \frac{E_1 - E_2}{\log(a_1/a_2)} \qquad (3).$$

The calculated constant c is also stored in the memory 23. It is to be noted that the calculation of the constant c is related to the calibration of the span. Since the span is hardly affected by the drift, the constant c need not be recalculated after it has been calculated once at the preparation stage of the measurement.

In this manner the preparation for the measurement of unknown ion concentrations of successive sample solutions has been completed. At this time there have been stored in the memory 23 the calculated constant c, the known ion concentration $a_k = a_1$ or $a_2$ and its related potential value $E_k = E_1$ or $E_2$ of one of the two standard solutions. In this example the known ion concentration $a_1$ of the first standard solution and the potential value $E_1$ corresponding to this ion concentration $a_1$ have been stored.

Then a sample solution whose ion concentration $a_x$ is to be measured is introduced in the vessel 13 and the two electrodes 11 and 12 are dipped in the solution. The potential difference $E_x$ then produced is applied to the arithmetic unit 16 after the conversion into a digital amount. Between the two values $a_x$ and $E_x$ the following relation exists, $$E_x = E_0 + c \log a_x \qquad (4).$$

From the two equations (1) and (4), the following equation is derived, $$E_x = E_1 - c \log a_1 + c \log a_x.$$

This equation leads to the following equation (5) as readily seen in the following processing.

$$a_x = 10^{\frac{E_x}{c}} \cdot 10^{\frac{E_1 - c \log a_1}{c}} \qquad (5)$$
$$= 10^{\frac{E_x}{c}} \cdot 10^{-\frac{E_1}{c}} \cdot a_1$$
$$= a_1 \cdot 10^{\frac{E_x - E_1}{c}}$$

In this manner the measured value of the unknown ion concentration $a_x$ can be obtained by effecting a calculation in accordance with the equation (5). To this end a switch 26 is closed to energize a control unit 27. The control unit 27 then commands the arithmetic unit 16 to calculate the value of the unknown ion concentration according to the equation (5) while supplying to the arithmetic unit 16 the known ion concentration $a_1$, the measured potential difference $E_1$ and the calculated constant c which have been stored in the memory 23. The calculated value of $a_x$ is displayed on the indicator 17 as a digital amount. This displayed value has been correctly calibrated in both the reference point and the span.

Although the span need not be calibrated frequently, it is preferable to recalibrate the reference point at a suitable time interval during the measurement of sample solutions, because the reference point might be affected by the drift. According to the present invention this recalibration of the reference point can be effected in such a simple manner that the two electrodes 11 and 12 are dipped in only the first standard solution and that the switch 20 is actuated to close the relay contact 22 for storing the produced new potential difference $E'_1$ in the memory 23 instead of the previously stored value $E_1$. It should be noted that at this time the constant c need not be recalculated.

By the recalculation according to the equation (5) by the use of said new $E'_1$ for $E_1$ a more correct value of the ion concentration $a_x$ can be obtained under the condition of recalibrated reference point. As seen from the equations (1), (2) and (4), the value of the ion concentration $a_x$ may be obtained in another manner. According to this method, at first the value of $E_0$ and c are calculated according to the equations (1) and (2) by the use of $E_1$ and $E_2$ obtained from the measurements for the first and second standard solutions, and then the calculated values of $E_0$ and c are applied to the corresponding terms of the equation (4) to obtain the value of an unknown ion concentration $a_x$ of a sample solution. However, this method requires the use of both the first and second standard solutions for recalibrating the reference point during a series of measurements, so that the method is troublesome for the recalibration of the reference point. On the contrary, the method according to the present invention by the use of the equation (5) is very simple since the present method requires the use of only one single standard solution for recalibrating the reference point during the measurement of sample solutions.

The apparatus according to the present invention is not only suitable for a manually operated apparatus for measuring ion concentration, but also suitable for an apparatus automated fully with the inclusion for pipetting a new solution and draining a waste sample solution, because the calibrations of the reference point and the span can be carried out by merely pressing the switches 20, 24 and 26. Moreover the apparatus according to the present invention allows the reference point to be recalibrated in a simple manner and short time because only one of the standard solutions is required for the recalibration during a series of measurements. Furthermore the apparatus according to the present invention allows easy and correct calibrations at the preparation stage. In contrast to conventional apparatus shown in FIG. 1, the manual adjustment of the adjuster 6 is required.

The present invention should not be restricted to the above embodiment. Many modifications and variations may be conceived within the scope of the present invention. For example, although the apparatus using only one ion electrode has been described, the present invention may be applied to an apparatus using a multiple of ion electrodes without changing any material point of the present invention; the features of the present invention, particularly that of handy calibration of the reference point and the span, are more advantageous to an apparatus having many test items. Moreover although in the above embodiment information is processed and stored in digital form with the aid of an analog-to-digital converter 15, an apparatus in analog form may be used where the analog-to-digital converter 15 is not used, an analog arithmetic unit is used as the arithmetic unit 16, an analog memory is used as the memory unit 23, potentiometers are used instead of preset-counters 18 and 19, and an analog indicator is used for the indicator 17. In such apparatus, only the indicator 17 may be constructed as a digital one. Furthermore although two standard solutions are used in the above embodiment, three or more standard solutions may be used for calculating a more precise value of the constant c to increase the accuracy and stability. For instance, a mean value of a plurality of calculated values of the constant c may be stored in the memory.

What is claimed is:

1. A method for calibrating an ion concentration measurement with the aid of at least first and second standard solutions having known different ion concentrations $a_1$ and $a_2$, respectively, comprising a step for detecting first and second potential values $E_1$ and $E_2$ corresponding to the known ion concentrations $a_1$ and $a_2$, respectively; a step for determining a constant c defined by an equation $$C = \frac{E_1 - E_2}{\log (a_1/a_2)}$$

with using said known ion concentrations $a_1$ and $a_2$ and detected potential values $E_1$ and $E_2$; a step for storing the calculated constant c, the known ion concentration $a_1$ of the first standard solution and its related potential value $E_1$; and a step for effecting a recalibration by detecting a new potential value $E_1'$ with using the first standard solution and replacing the previously stored potential value $E_1$ by the newly detected potential value $E_1'$.

2. A method according to claim 1, wherein at least three potential values are detected with using at least three standard solutions having known different ion concentrations, and a mean value of at least two constants calculated with using said detected potential values and known ion concentrations is stored as the constant c.

3. An apparatus for calibrating an ion concentration measurement with the aid of at least first and second standard solutions having known different ion concentrations $a_1$ and $a_2$ and detected potential values $E_1$ and $E_2$ corresponding to said known ion concentrations $a_1$ and $a_2$, respectively, comprising: means for presetting said known ion concentrations $a_1$ and $a_2$, means for calculating a constant c defined by an equation $$C = \frac{E_1 - E_2}{\log(a_1/a_2)}$$

with using the preset ion concentrations $a_1$ and $a_2$ and the detected potential values $E_1$ and $E_2$, means for storing the calculated constant c, the ion concentration $a_1$ of the first standard solution and its related potential value $E_1$, and means for effecting a recalibration by replacing said stored potential value $E_1$ by a newly detected potential value $E_1'$ for the first standard solution.

4. An apparatus according to claim 3, further comprising an analog-to-digital converter for converting the detected potential values $E_1$, $E_2$ and $E_1'$ into a digital form, while said presetting means is formed by a preset counter.

5. An apparatus according to claim 4, including switching means between said analog-to-digital converter and said storing means so as to exclusively supply the detected potential values $E_1$, $E_2$ and $E_1'$ for the standard solutions to the storing means.

6. An apparatus according to claim 5, further comprising switching means for operating the calculator to calculate the constant c.

* * * * *